United States Patent
Shrivastava et al.

(10) Patent No.: US 12,046,363 B2
(45) Date of Patent: Jul. 23, 2024

(54) SCALABLE FILTERING INFRASTRUCTURE FOR VARIABLE CONTROL RATES IN A DISTRIBUTED SYSTEM SUCH AS A SURGICAL ROBOTIC SYSTEM

(71) Applicant: Verb Surgical Inc., Santa Clara, CA (US)

(72) Inventors: Apoorv Shrivastava, Santa Clara, CA (US); Haoran Yu, Santa Clara, CA (US); Renbin Zhou, Santa Clara, CA (US); H. Tutkun Sen, Santa Clara, CA (US); Alireza Hariri, Santa Clara, CA (US)

(73) Assignee: Verb Surgical Inc., Santa Clara, CA (US)

( * ) Notice: Subject to any disclaimer, the term of this patent is extended or adjusted under 35 U.S.C. 154(b) by 453 days.

(21) Appl. No.: 17/366,237

(22) Filed: Jul. 2, 2021

(65) Prior Publication Data
US 2023/0005610 A1 Jan. 5, 2023

(51) Int. Cl.
| | |
|---|---|
| H03H 7/30 | (2006.01) |
| A61B 34/10 | (2016.01) |
| A61B 34/37 | (2016.01) |
| B25J 9/16 | (2006.01) |
| G16H 40/63 | (2018.01) |

(Continued)

(52) U.S. Cl.
CPC .............. *G16H 40/63* (2018.01); *A61B 34/10* (2016.02); *A61B 34/37* (2016.02); *B25J 9/1605* (2013.01); *A61B 2034/101* (2016.02)

(58) Field of Classification Search
CPC ........ G16H 40/63; A61B 34/37; A61B 34/10; A61B 2034/101; B25J 9/1605; H04B 1/001

USPC ................................ 375/350, 229, 232, 235
See application file for complete search history.

(56) References Cited

U.S. PATENT DOCUMENTS

| | | | |
|---|---|---|---|
| 2006/0133551 A1* | 6/2006 | Davidoff | H04B 1/001 375/350 |
| 2019/0176334 A1 | 6/2019 | Zhou et al. | |
| 2019/0254761 A1 | 8/2019 | Sen et al. | |

(Continued)

FOREIGN PATENT DOCUMENTS

| | | |
|---|---|---|
| JP | 2017513539 A | 6/2017 |
| KR | 20120099752 A | 9/2012 |

(Continued)

OTHER PUBLICATIONS

The International Search Report and Written Opinion of the International Searching Authority for International Application No. PCT/IB2022/055438 Mailed Sep. 19, 2022.

(Continued)

*Primary Examiner* — Phuong Phu
(74) *Attorney, Agent, or Firm* — Lempia Summerfield Katz LLC (57) ABSTRACT

For a scalable filtering infrastructure, a library of filters each usable at different control rates is provided by defining filters in a continuous time mode despite eventual use for digital filtering. For implementation, a filter is selected and discretized for the desired control rate. The discretized filter is then deployed as a discrete time realization for convolution. In a distributed system with multiple control rates, the library may be used to more rapidly and conveniently generate the desired filters.

20 Claims, 4 Drawing Sheets

(51) Int. Cl.
    *H03H 7/40*         (2006.01)
    *H03K 5/159*       (2006.01)

(56)           References Cited

U.S. PATENT DOCUMENTS

| | | |
|---|---|---|
| 2020/0060777 A1 | 2/2020 | Nowlin et al. |
| 2021/0007812 A1 | 1/2021 | Zhou et al. |
| 2021/0016445 A1 | 1/2021 | Zhou et al. |
| 2021/0045827 A1 | 2/2021 | Asadian et al. |
| 2021/0085407 A1 | 3/2021 | Sen et al. |
| 2021/0121257 A1 | 4/2021 | Yu |

FOREIGN PATENT DOCUMENTS

| | | |
|---|---|---|
| KR | 20150003290 A | 1/2015 |
| KR | 20200031081 A | 3/2020 |

OTHER PUBLICATIONS

Cunningham, Alexander, et al. "Fully distributed scalable smoothing and mapping with robust multi-robot data association." 2012 IEEE International Conference on Robotics and Automation. IEEE, 2012. pp. 1093-1100.

* cited by examiner

SCALABLE FILTERING INFRASTRUCTURE FOR VARIABLE CONTROL RATES IN A DISTRIBUTED SYSTEM SUCH AS A SURGICAL ROBOTIC SYSTEM

FIELD

Embodiments relate to scalable filtering for design and/or use in a surgical robotic system or other system.

BACKGROUND

Surgical robotic systems give an operating surgeon the ability to robotically perform one or more actions of a surgical procedure. In the surgical robotic system, a robot manipulates a surgical tool to assist in surgery. A user console receives user input to control the robot and may be posited remotely from the robot. A control tower may communicatively connect between the user console and the robot. These distributed components have different signal or data filtering requirements. To complicate the filtering, the different components may provide data for filtering at different sampling rates. Due to different modes of operation, a given component may operate at different rates. The active components of the system change depending on the various system and/or sub-system modes, such as clinical mode (i.e., surgery), training or simulation mode, or standalone (e.g., active system fault state due to loss of communications). In these modes, system functionality is often duplicated to meet operational requirements or is redundantly implemented for fault detection or fault handling. Depending on hardware specifications or computational limitations, the various underlying control algorithms implemented as firmware or software may need to run at various different control rates. As a result, it is difficult and time consuming to design filters appropriate for the various signals at the different control rates.

SUMMARY

By way of introduction, the preferred embodiments described below include methods, systems, instructions, and computer readable media for a scalable filtering infrastructure. By defining filters in a continuous time mode despite eventual use for digital filtering, a library of filters each usable at different control rates is provided. For implementation, a filter is selected and discretized for the desired control rate. The discretized filter is then deployed as a discrete time realization for convolution. In a distributed system with multiple control rates, the library may be used to more rapidly and conveniently generate the desired filters.

In a first aspect, a method is provided for filtering information in a surgical robotic system. A library of filters defined as continuous domain transfer functions is generated. A first of the filters is discretized based on a sample rate for the information in the surgical robotic system. The information is filtered at the sample rate. The filtering includes convolving the information with a linear system realization of the first of the filters. The surgical robotic system is operated, such as operating in any of various modes, with the filtered information.

In a second aspect, a surgical robotic system is provided for filtering at different control rates. A surgical robot has a first component operable at a first control rate. A user console is configured to receive user input for control of the surgical robot. The user console connects wirelessly or through wires to the surgical robot. The user console has a second component operable at a second control rate different than the first control rate. A memory stores a library of filters defined in a continuous domain. A processor is configured to discretize a first filter from the library with the first control rate and a second filter from the library with the second control rate. The processor is configured to generate discrete time realizations of the first and second filters.

In a third aspect, a method is provided for a scalable filtering infrastructure. Filter requirements for filtering at a first control rate are input. A filter is generated from a library of filters based on the requirements. The filters of the library are independent of the first control rate. The selected filter is converted to the first control rate. A filter kernel is generated for the converted filter. Signals are filtered with the filter kernel at the first control rate.

The present invention is defined by the following claims, and nothing in this section should be taken as a limitation on those claims. Further aspects and advantages of the invention are discussed below in conjunction with the preferred embodiments and may be later claimed independently or in combination.

BRIEF DESCRIPTION OF THE DRAWINGS

The embodiments of the invention are illustrated by way of example and not by way of limitation in the figures of the accompanying drawings in which like references indicate similar elements. It should be noted that references to "an" or "one" embodiment of the invention in this disclosure are not necessarily to the same embodiment, and they mean at least one. Also, in the interest of conciseness and reducing the total number of figures, a given figure may be used to illustrate the features of more than one embodiment of the invention, and not all elements in the figure may be required for a given embodiment.

DETAILED DESCRIPTION

A scalable software infrastructure supports variable control rates for reconfigurable hardware and/or software. In order to address different modes of operation and a distributed system, a continuous-time filter library is provided with discretization methods that allow software to be run at various different control rates while maintaining transient and steady state system response and/or performance.

In one embodiment, the filtering process is split into three stages. In a first stage, filter definitions and corresponding performance requirements are used to generate the library. A user or developer defines the required system characteristics for filtering in software or hardware. These include but are not limited to transfer function types, cut-off frequencies, attenuation, bandwidth, order, etc. The filters for these requirements are converted into s-domain transfer functions. Alternatively, a s-domain transfer function is directly specified. The result is a library of filters defined in continuous time. In a second stage, one or more of the filters are discretized. Depending on the specified control rate of the software process and the intended application, a discretized z-domain transfer function is generated from a selected filter of the library. In a third stage, a standard controllable or observable realization or a custom realization is generated, depending on the context. For filter deployment or realization, the discretized filter is used to generate a discrete time realization that can perform signal filtering as desired. In certain real time contexts, the filter may be required to meet additional requirements of minimal dynamic memory allocation at runtime. The order of the filter selected may be used to control the memory allocation.

The formation of the continuous-time filters of the library with discretization to particular control rates supports multiple control rates across different system (hardware and/or software) configurations. The continuous-time library separates the mathematical definition of a discrete filter from its real time context usage. Validation of filter parameters, including stability at specified control rates, may be enabled through use of the library to test different filters for a given context. The library infrastructure with discretization to control rates needed for particular realization may reduce the number of control parameters and tuning effort for robotics or control engineers. Since the definition of the filters is separated from the context, requirements for defined filters may be accurately recorded.

Figure 1:
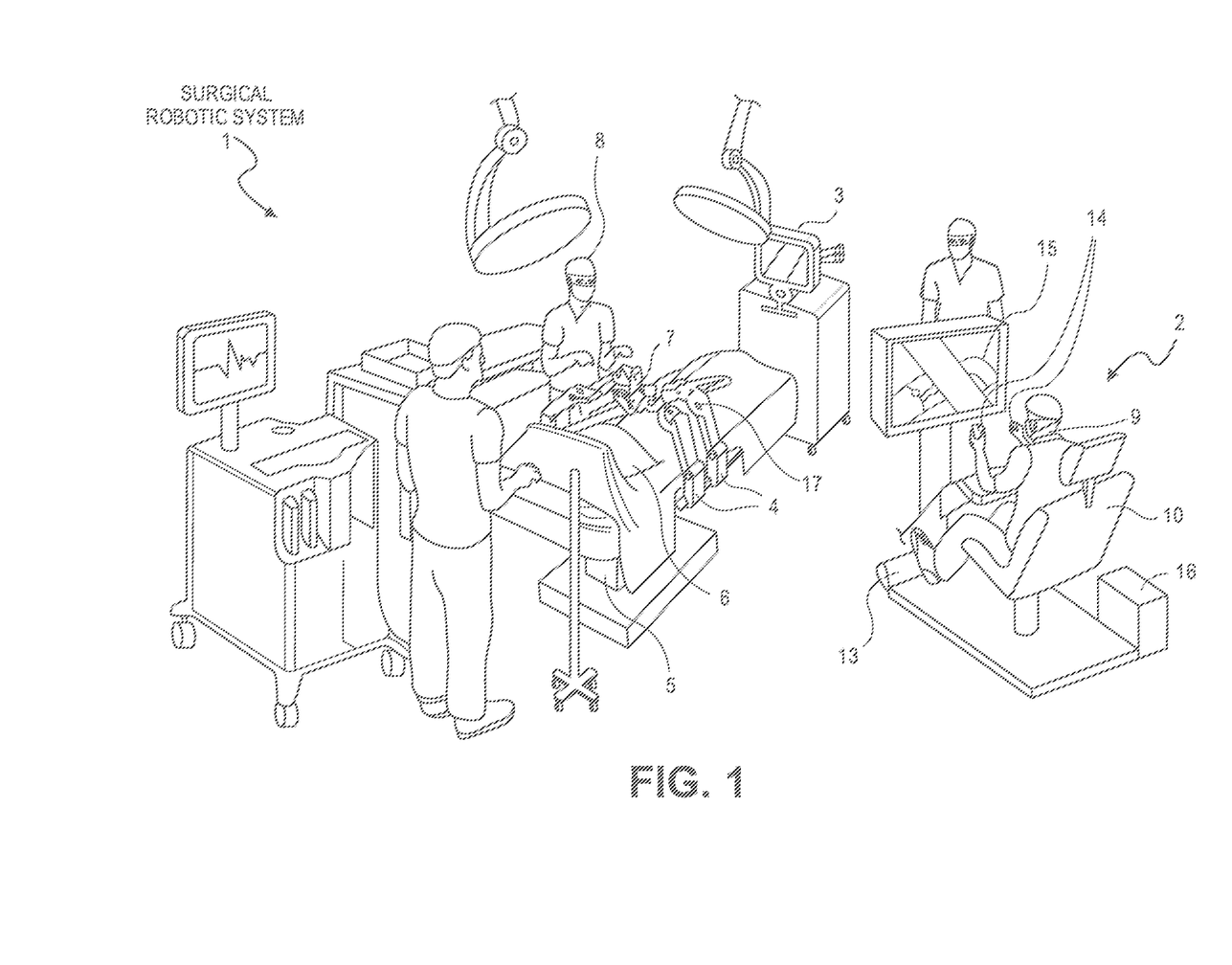
FIG. 1 is a pictorial view of an example surgical robotic system in an operating arena.

FIG. 1 shows an example surgical robotic system. The surgical robotic system is a distributed system and includes multiple modes of operation, both of which result in use of different filters (e.g., for different components and/or for different modes of operation) in the one system. FIG. 1 is provided as an example environment for which the filter infrastructure is used. In other embodiments, other distributed systems and/or other systems with multiple modes of operation may be provided, whether robotic or not, whether medical or not. In alternative embodiments, a single processor operating in one mode uses filtering at more than one control rate, so the filter infrastructure is used to realize different filters for or by the processor.

Figure 2:
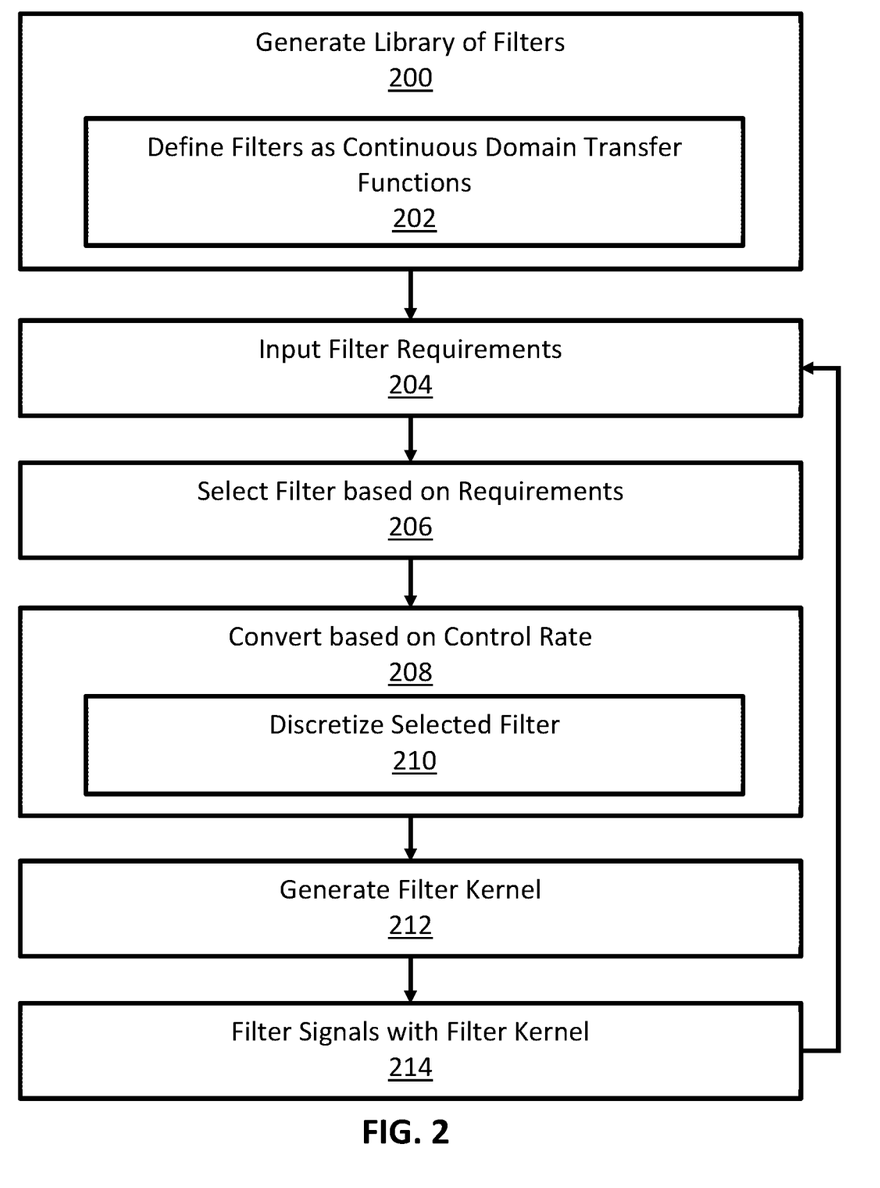
FIG. 2 is a flow diagram of one embodiment of a method for implementing a scalable filter infrastructure.
Figure 3:
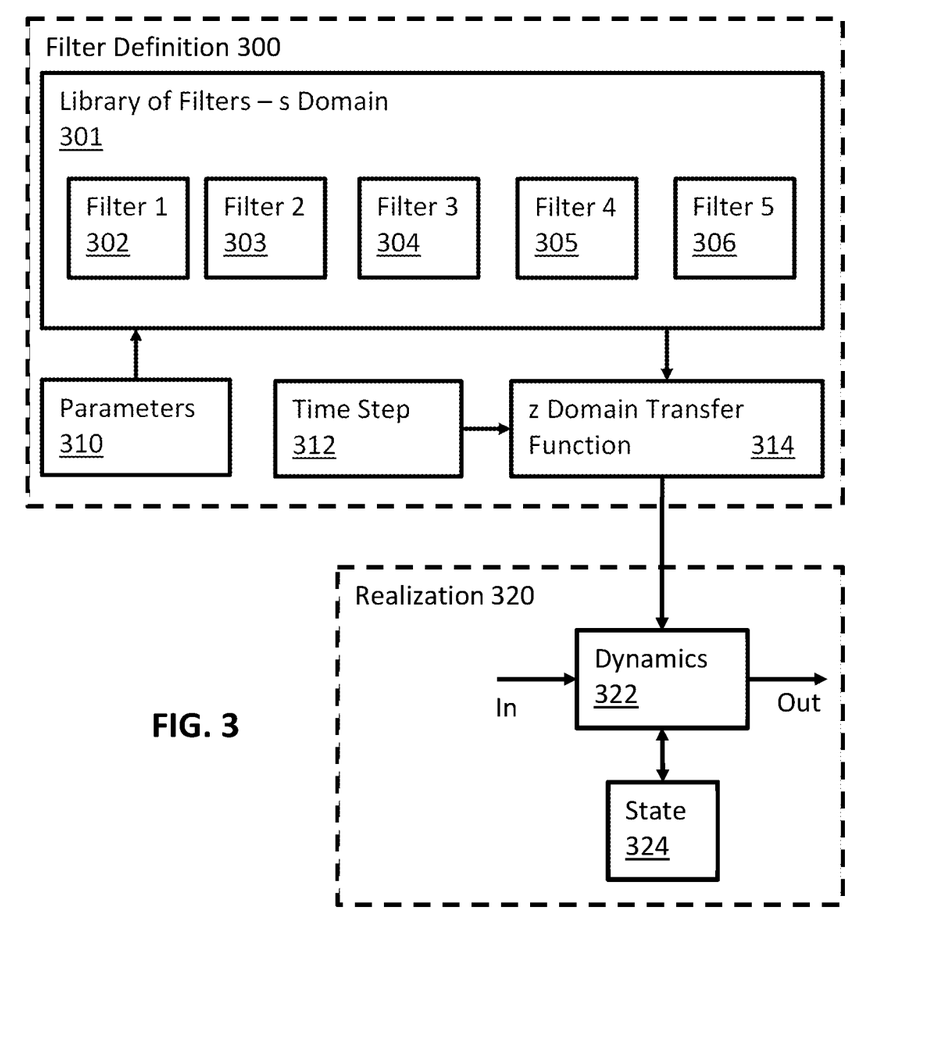
FIG. 3 illustrates a scalable filter infrastructure.
Figure 4:
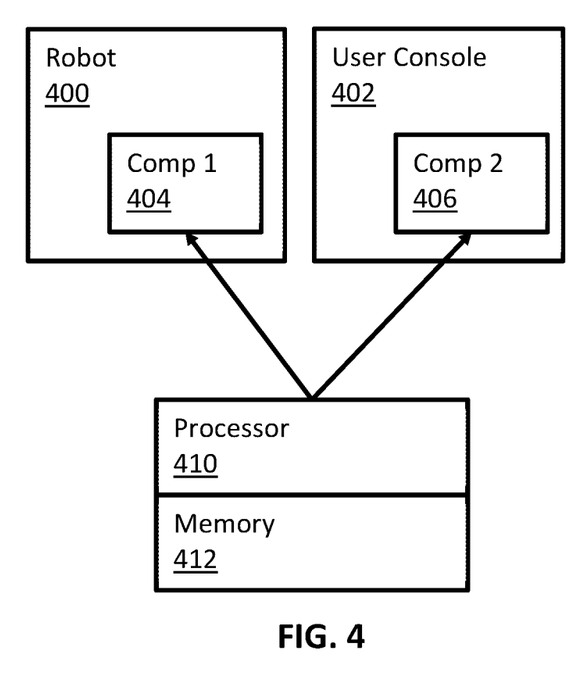
FIG. 4 is a block diagram of one embodiment of a robotic system using the scalable filter infrastructure.

FIG. 2 shows a method using the filter infrastructure, and FIG. 3 shows an example representation of the filter infrastructure. FIG. 4 shows an example generalized distributed system for using the filter infrastructure, albeit in a robotic context.

FIG. 1 is a pictorial view of an example surgical robotic system 1 in an operating arena. The surgical robotic system 1 includes a user console 2, a control tower 3, and one or more surgical robotic arms 4 at a surgical platform 5, e.g., a table, a bed, etc. The surgical robotic system 1 can incorporate any number of devices, tools, or accessories used to perform surgery on a patient 6. For example, the surgical robotic system 1 may include one or more surgical tools 7 used to perform surgery. The surgical tool 7 may have an end effector at its distal end (also a distal end of the robotic surgical arm 4 to which the surgical tool 7 is attached), for executing a surgical operation such as stapling, cutting, grasping, poking, or energy emission.

Each surgical tool 7 may be manipulated manually, robotically, or both, during the surgery. For example, the surgical tool 7 may be a tool used to enter, view, or manipulate an internal anatomy of the patient 6. The surgical tool 7 may be controlled manually, directly by a hand of a bedside operator 8; or it may be controlled robotically, via sending electronic commands to actuate movement of the surgical robotic arm 4 to which the surgical tool 7 is attached. The surgical robotic arms 4 are shown as a table-mounted system, but in other configurations the surgical robotic arms 4 may be mounted in a cart, ceiling or sidewall, or in another suitable structural support.

Generally, a remote operator 9, such as a surgeon, may use the user console 2 to remotely manipulate the surgical robotic arms 4 and the attached surgical tools 7, e.g., teleoperation. The user console 2 may be located in the same operating room as the rest of the surgical robotic system 1, as shown in FIG. 1. In other environments however, the user console 2 may be located in an adjacent or nearby room, or it may be at a remote location, e.g., in a different building, city, or country. The user console 2 may include a seat 10, foot-operated controls 13, one or more handheld user interface devices, UID 14, and at least one user display 15 that is configured to display, for example, a view of the surgical site inside the patient 6. In the example user console 2, the remote operator 9 is sitting in the seat 10 and viewing the user display 15 while manipulating a foot-operated control 13 and a handheld UID 14 in order to remotely control the surgical robotic arms 4 and the surgical tools 7 (that are mounted on the distal ends of the surgical arms 4).

In some variations, the bedside operator 9 may also operate the surgical robotic system 1 in an "over the bed" mode, in which the beside operator 8 (user) is now at a side of the patient 6 and is simultaneously manipulating i) a robotically-driven tool (having an end effector) that is attached to the surgical robotic arm 4, e.g., with a handheld UID 14 held in one hand, and ii) a manual laparoscopic tool. For example, the bedside operator's left hand may be manipulating the handheld UID to control a surgical robotic component, while the bedside operator's right hand may be manipulating a manual laparoscopic tool. Thus, in these variations, the bedside operator 8 may perform both robotic-assisted minimally invasive surgery and manual laparoscopic surgery on the patient 6.

During an example procedure (surgery), the patient 6 is prepped and draped in a sterile fashion to achieve anesthesia. Initial access to the surgical site may be performed manually while the arms of the surgical robotic system 1 are in a stowed configuration or withdrawn configuration (to facilitate access to the surgical site.) Once access is completed, initial positioning or preparation of the surgical robotic system 1 including its surgical robotic arms 4 may be performed. Next, the surgery proceeds with the remote operator 9 at the user console 2 utilizing the foot-operated controls 13 and the UIDs 14 to manipulate the various end effectors and perhaps an imaging system to perform the surgery. Manual assistance may also be provided at the procedure bed or table, by sterile-gowned bedside personnel, e.g., the bedside operator 8 who may perform tasks such as retracting tissues, performing manual repositioning, and tool exchange upon one or more of the surgical robotic arms 4. Non-sterile personnel may also be present to assist the remote operator 9 at the user console 2. When the procedure or surgery is completed, the surgical robotic system 1 and the user console 2 may be configured or set in a state to facilitate post-operative procedures such as cleaning or sterilization and healthcare record entry or printout via the user console 2.

In one embodiment, the remote operator 9 holds and moves the UID 14 to provide an input command to move a robot arm actuator 17 in the surgical robotic system 1. The UID 14 may be communicatively coupled to the rest of the surgical robotic system 1, e.g., via a console computer system 16. The UID 14 can generate spatial state signals corresponding to movement of the UID 14, e.g. position and orientation of the handheld housing of the UID, and the spatial state signals may be input signals to control a motion of the robot arm actuator 17. The surgical robotic system 1 may use control signals derived from the spatial state signals, to control proportional motion of the actuator 17. In one embodiment, a console processor of the console computer system 16 receives the spatial state signals and generates the corresponding control signals. Based on these control signals, which control how the actuator 17 is energized to move a segment of the surgical robotic arm 4, the movement of a corresponding surgical tool that is attached to the arm may mimic the movement of the UID 14. Similarly, interaction between the remote operator 9 and the UID 14 can generate for example a grip control signal that causes a jaw of a grasper of the surgical tool 7 to close and grip the tissue of patient 6.

The surgical robotic system 1 may include several UIDs 14, where respective control signals are generated for each UID 14 that control the actuators and the surgical tool (end effector) of a respective surgical robotic arm 4. For example, the remote operator 9 may move a first UID 14 to control the motion of an actuator 17 that is in a left robotic arm, where the actuator responds by moving linkages, gears, etc., in that surgical robotic arm 4. Similarly, movement of a second UID 14 by the remote operator 9 controls the motion of another actuator 17, which in turn moves other linkages, gears, etc., of the surgical robotic system 1. The surgical robotic system 1 may include a right surgical robotic arm 4 that is secured to the bed or table to the right side of the patient, and a left surgical robotic arm 4 that is at the left side of the patient. An actuator 17 may include one or more motors that are controlled so that they drive the rotation of a joint of the surgical robotic arm 4, to for example change, relative to the patient, an orientation of an endoscope or a grasper of the surgical tool 7 that is attached to that arm. Motion of several actuators 17 in the same surgical robotic arm 4 can be controlled by the spatial state signals generated from a particular UID 14. The UIDs 14 can also control motion of respective surgical tool graspers. For example, each UID 14 can generate a respective grip signal to control motion of an actuator, e.g., a linear actuator, that opens or closes jaws of the grasper at a distal end of surgical tool 7 to grip tissue within patient 6. One or more of the UIDs 14 can also control motion of a stapler, such as activating the application of a staple to the tissue of the patient 9.

In some aspects, the communication between the surgical platform 5 and the user console 2 may be through a control tower 3, which may translate user commands that are received from the user console 2 (and more particularly from the console computer system 16) into robotic control commands that are transmitted to the surgical robotic arms 4 on the surgical platform 5. The control tower 3 may also transmit status and feedback from the surgical platform 5 back to the user console 2. The communication connections between the surgical platform 5, the user console 2, and the control tower 3 may be via wired and/or wireless links, using any suitable ones of a variety of data communication protocols. Any wired connections may be optionally built into the floor and/or walls or ceiling of the operating room. The surgical robotic system 1 may provide video output to one or more displays, including displays within the operating room as well as remote displays that are accessible via the Internet or other networks. The video output or feed may also be encrypted to ensure privacy and all or portions of the video output may be saved to a server or electronic healthcare record system.

Any of the various components of the surgical robotic system may generate, operate on, or receive signals to be filtered. A processor or other digital hardware is programmable to implement the desired filtering. In a distributed system like this example robotic surgical system, there may be tens or hundreds of different filters to be implemented. Where the system may operate in different modes, the same signals may be filtered differently, even at a different control rate. The sample rates used by different components (e.g., processors or other hardware) and/or for different modes may require even more filters to be defined. Separately design filter kernels for all these filters is time consuming and difficult.

FIG. 2 is a flow chart diagram of one embodiment of a method for creating and use of a scalable filtering infrastructure. The filtering process is split into three stages, filter definition in a library, discretization, and realization. One or more filters are generated for use by one or more components and/or modes of operation. In one example use, FIG. 2 shows a method for filtering information in a surgical robotic system.

The method is implemented by a processor, such as a computer, workstation, or server. The implementation of realized filters may be performed by one or more other processors, such as a processor implementing software filtering or programmable hardware implementing filtering. For example, acts 200-212 are performed by a computer. Different computers may be used at different times and/or for different acts of the method, such as one computer for acts 200 and 202, and a different computer for acts 204-212. In this example, act 214 is performed by a component of a distributed or other system.

The acts are performed in the order shown (e.g., top to bottom or numerical) or a different order. For example, the filter is selected in act 206 based on other criteria (e.g., user selects desired type of filter), and then the requirements for the selected filter are input in act 204.

Additional, different, or fewer acts may be provided. For example, acts 200 and/or 202 are not performed where the library already exists or the user chooses to directly specify the discrete transfer function. In yet another example, acts 200 and 202 are performed without the other acts to create the library of continuous-time filters.

In act 200, a processor or processors generate a filter. The filter is generated alone or generated with other filters in a library of filters. A user or developer defines the required system characteristics. The characteristics include but are not limited to transfer function types, cut-off frequencies, attenuation, bandwidth, order, etc. Filters with different characteristics are defined. The definitions may be formed by a search or randomization or may be characteristics needed for a particular system. Sets of characteristics defining multiple different filters are input.

In one embodiment, the transfer function types are used to define a generic filter for each type. The bandwidth, cut-off frequencies, attenuation, and/or other characteristics are not defined as the generic filter may be configured to provide different bandwidths, cut-off frequencies, attenuation, and/or other characteristics. Any sub-set or all characteristics may be used to define a filter for the library.

The filters are defined as time-continuous filters in act 202. The library is generated as a library of filters defined as continuous domain transfer functions. The defined filters are converted into s-domain transfer functions, such as using Laplace domain processing. Alternatively, the definition may directly specify an s-domain transfer function. The filter definitions based on requirements are translated into the continuous domain transfer functions. Alternatively, act 204 is performed prior to act 202, which is a conversion of the defined filters into time-continuous filters.

The time-continuous filters, such as provided by the s-domain transfer functions, are independent of the sampling rate. By defining the filters as time-continuous (e.g., analog), the sampling rate is not used in the definition.

In one embodiment, the definitions are by type of filter. The library is generated to include filters of different types. For example, the library, H(s) in the s-domain, is represented as:

$$H(s) = \begin{cases} f_{chebyshev}(w_n, \tau_n, \ldots) \\ f_{notch}(w_n, w_b, \ldots)) \\ \cdot \\ \cdot \\ \cdot \\ f_{ctf} = \dfrac{Y(s)}{X(s)} \end{cases}$$

where f is the filter, the parameters in parenthesis are the variables for the filter, and the subscript is the type of transfer function where "ct" is custom.

In generation of the transfer functions, filter definitions specify the filter parameters such as cutoff frequencies, amplitude response graph slopes, etc. These definitions are translated into continuous domain (s-domain) transfer functions. Some example filters as s-domain transfer functions include Butterworth, Chebyshev Type II, Notch, $2^{nd}$ Order, and custom filters. The Butterworth filter is parameterized by the cutoff frequency ($W_n$) and order (n), where the method of discretization is the bilinear transform. The s-domain transfer function is given as:

$$H_{butterworth} = \dfrac{\omega^n}{\prod_{i=1}^{n/2} s^2 - 2\cos\left(\dfrac{2i+n-1}{2n}\pi\right)s + \omega^2}.$$

The s-domain transfer function for the Chebyshev Type II filter is given by:

$$H_{chbyII} = \dfrac{\prod_{i=1}^{n/2} s^2 + \left(\dfrac{w}{\cos\dfrac{2i-1}{2n}\pi}\pi\right)^2}{\prod_{i=1}^{n/2} s^2 + 4w\,\sinh(\lambda)\cos\dfrac{\theta_i}{2}c_i s + 2c_i w^2} H_n(s)$$

$$\theta_i = \dfrac{n+1-2i}{n}\pi \quad c_i = \dfrac{1}{\cosh 2\lambda - \cos\theta_k} \quad \lambda = \dfrac{\sin^{-1}(1/\eta)}{n}$$

$$H_n = \begin{cases} 1 & n = 2k \\ s + \dfrac{w}{\sinh\lambda} & n = 2k+1 \end{cases}.$$

The s-domain transfer function for the notch filter is given by:

$$H_{notch} = \dfrac{s^2 + \omega_c^2}{s^2 + s\omega_b + \omega_c^2}.$$

The s-domain transfer function of the $2^{nd}$ order filter is given by:

$$H_{2nd-order} = \dfrac{\omega_n^2}{s^2 + 2\tau\omega_n + \omega_n^2}.$$

An example s-domain transfer function of a custom filter is given by:

$$H_{custom} = \dfrac{\sum_{i=0}^{n} a_i s^i}{\sum_{i=0}^{n} b_i s^i}.$$

Other types of filters may be used. Multiple filters of the same type may be defined, such as where one or more variables in the s-domain transfer function are set or defined.

The resulting set, H(s), of time-continuous filters provides a defined library of filters. FIG. 3 shows an example. The filter definition 300 includes the library 301 of filters 302-306. Any number of filters may be defined.

Once the library is created, other filters may be defined and added. As new requirements from a new mode, component, and/or signal are found, new filters may be added to the library 301.

Once the library 301 is created, the library 301 is used to create a filter for a given component and/or signal. Referring to FIG. 2, the filter requirements for the filter to be created are input in act 204. The filter requirements, such as the bandwidth, cut-off frequency, transfer function type, attenuation, order, and/or other characteristic of the filter or the signal (e.g., data stream) to be filtered are input.

The order of the filter may be limited. For example, memory space for a given component implementing the filter may be limited. The order of the filter may be likewise limited to avoid exceeding available memory.

The component and/or signal for which the filter is to be used has a given control rate. The sample rate or rate of processing the filter may be different for different components, modes, and/or signals. Since the filter is to be realized for software filtering or filtering by programmable hardware, the signals to be filtered are digital signals have a given sampling rate. The filter requirements include the control or sample rate.

The designer, engineer, or other user inputs the filter requirements. The input may be through selection of the filter in act 206 or through providing values for one or more variables.

In act 206, the processor selects or generates the filter 302-306, such as from the library 301, based on filtering requirements. The requirements may result in identification of one filter 302-306 of the library. For example, one filter type is identified, and that type is specialized based on the requirements of the user. Alternatively, multiple filters 302-306 are identified.

The identified filters 302-306 matching the requirements are output, such as in a list. The user may then select a specific one of the filters 302-306. Alternatively, the processor identifies one of the filters 302-306 based on any criterion, such as least memory usage, from amongst the filters 302-306 that satisfy the requirements. The realization provides flexibility by, for example, memory reduction where the input version requires ~2n memory whereas the canonical version require ~n memory. In other embodiments, the user selects the filter 302-306 without processor selection.

The selected filter (e.g., filter 306) is in the continuous time domain. In act 208, the processor converts the filter based on the control rate. In act 210, the conversion discretizes the selected filter to operate at the control rate. Since the filter will be operated in a digital environment on samples or data at a given rate, the filter is discretized to operate at that rate. The selected filter is converted from the continuous time domain to a discrete time domain in order to operate at the control rate. For filter discretization, the continuous time transfer function generated from filter definitions is mapped to a discrete time transfer function. The sample or control rate for the information to be filtered is used to discretize the filter. In one embodiment, a z-domain transfer function is formed as the discrete time transfer function. The z-domain transfer function is formed at the sample rate.

Depending on the specified control rate of the software process and the intended application, a discretized z-domain transfer function, H(z), is generated, as represented by:

$$H(z) = \begin{cases} f_{bilinear}(H(s), \psi_{bilinear}) \\ f_{matched}(H(s)) \\ f_n\text{-hold}(H(s), \psi_{hold}) \end{cases}$$

where bilinear, matched, and n-hold are types of substitutions of the continuous time variable, s, with discrete time variable, z. Any substitution may be used, such as bilinear, bilinear with prewarp, or matched substitution of a continuous time variable of the filter.

In one example embodiment of discretization of the filter, $\Delta T$ is a hardware and/or software-mode specific parameter representing the nominal control rate or update period of the signal to be processed. For bilinear substitution, $$s = \frac{2}{\Delta T} \frac{z-1}{z+1}$$

in the continuous time transfer function. For bilinear with frequency prewarp, $$s = \frac{\frac{2\pi}{\Delta T_p}}{\tan\left(\frac{\pi \Delta T}{\Delta T_p}\right)} \frac{z-1}{z+1}$$

in the continuous time transfer function where $\Delta T_p$, is the prewarp compensation timestep. For matched substitution, the discrete time transfer function is generated after mapping the poles and zero of the continuous time transfer function through the mapping $z=e^{s\Delta T_s}$. In general, the discretization maps the filter definition to the discrete rate specific form, represented as:

$$H(z) = \frac{\sum_{i=0}^{m} \beta_i s^i}{1 + \sum_{i=1}^{n} \alpha_i s^i}.$$

Other substitutions may be used.

FIG. 3 represents the discretization into a z-domain transfer function 314. The time step 312 to be applied for a given filter in a given context (e.g., for the selected filter running on particular hardware and/or for filtering a particular signal) is used to discretize to the digital domain, creating the z-domain transfer function 314.

Depending on the context, the controllable or observable realizations or a custom realization are generated in act 212. The processor generates a filter kernel for the converted filter. The discretized filter is realized. To instantiate the discretized filter, the filter kernel is created.

In one embodiment, a linear system realization is performed on the discrete time domain. For filter deployment or realization, the discrete time realization is transformed to perform signal filtering as desired. The discrete rate form may be realized using linear system realization techniques, resulting in a filter kernel that may be convolved with the incoming signal.

Example linear system realization techniques include the controllable technique, represented as:

$$A = \begin{bmatrix} 0 & 1 & 0 & \ldots & 0 \\ 0 & 0 & 1 & \ldots & 0 \\ \vdots & \vdots & \vdots & \ldots & \vdots \\ 0 & 0 & 0 & \ldots & 1 \\ -\alpha_n & -\alpha_{n-1} & -\alpha_{n-2} & \ldots & -\alpha_1 \end{bmatrix} \quad B = \begin{bmatrix} 0 \\ 0 \\ 0 \\ \vdots \\ 1 \end{bmatrix}$$

$$C = [\beta_n - \alpha_n\beta_0 \, \beta_{n-1} - \alpha_{n-1}\beta_0 \ldots \beta_1 - \alpha_1\beta_0] \quad D = \beta_0.$$

Another example technique results in the observable form, represented as:

$$A = \begin{bmatrix} 0 & 0 & 0 & \ldots & 0 & -\alpha_n \\ 1 & 0 & 0 & \ldots & 0 & -\alpha_{n-1} \\ 0 & 1 & 0 & \ldots & 0 & -\alpha_{n-2} \\ \vdots & \vdots & \vdots & \ldots & \vdots & \vdots \\ 0 & 0 & 0 & \ldots & 1 & -\alpha_1 \end{bmatrix} \quad B = \begin{bmatrix} \beta_n - \alpha_n\beta_0 \\ \beta_{n-1} - \alpha_{n-1}\beta_0 \\ \vdots \\ \beta_1 - \alpha_1\beta_0 \end{bmatrix}$$

$$C = [0 \; 0 \; \ldots \; 1] \quad D = \beta_0.$$

Yet another technique is the time series or input-output form, represented as:

$$y[k] = \sum_{i=0}^{n} \beta_i u[k-i] - \sum_{i=1}^{n} \alpha_i y[k-i].$$

Other techniques may be used.

In some real time contexts, the filter may be required to meet an additional requirement of minimal dynamic memory allocation at runtime. This requirement is met based on the order of the filter. By including the order as a limitation in selection of the filter, the realization may use a limited amount of memory.

In act 214, the processor or component of the system filters information at the sample rate. The realized filter is stored in a memory accessible by a component of the system, such as the surgical robotic system. Alternatively, a processor of the component creates and applies the realization. The processor or other hardware of a component of the distributed or other system implements the filtering using the realized filter, such as convolving in the controllable, observable, time series with input-output form, or another linear realization.

The realized filter (e.g., filter kernel) is convolved with the signal or data. The linear system realization is used to filter the signals. The filtering occurs at the control rate for that component. FIG. 3 shows an example of the realization 320. The realized filter is provided for dynamic operation 322. The signal is input, and a filtered signal is output. The state 324 represents the state of the dynamic filtering. The generated z domain transfer function represents a kernel that needs to be applied (e.g., multiplied) through a convolution to the signal (e.g., data) sampled periodically at the control rate for that component. To do this, a realization object 320 is created with dynamics 322 derived from the z-domain transfer function 314. The signal is an input to the realization at runtime and updates the internal state 324 of the realization through its input dynamics. Simultaneously, the state 324 is processed through the output dynamics to generate the output or filtered signal In one embodiment, the filtering uses shift operation. The linear system realization is implemented with shift operations in place of the matrix or kernel multiplications with the block identity matrix. Certain realizations have spare dynamics with at least part of the dynamics matrix being an identity matrix. These realizations allow shift operations to reduce the computational complexity through shift operations.

The filtered information is used to operate the system. In the surgical robotic system example, the filtered information is used in control, feedback, sensing, or other processing. The filtered information may be used in one or more modes of operation. The filter is operable at the control rate. Where the mode changes the control rate, a different discretization and realization is used.

Referring to FIG. 2, the feedback from act 214 to act 204 represents use of the library to generate and use a filter for another component, signal, and/or mode. The library is used again. A second filter of the library is selected 206 based on input 204 requirements. This selected filter is discretized 210 using the control rate for the context of the filter. After realization 212, this other filter is used to filter 214 signals, which signals are used in operation of the system. With a distributed system having different components with different control rates and/or a system with different modes using different control rates, the library of time-continuous filters is used to create various realized filters for digital filtering. Filters are created for different modes and/or components operating at different control rates. Alternatively, the feedback is for iterative designing of a filter.

FIG. 4 shows a block diagram of one embodiment of robotic system (e.g., surgical robotic system) for filtering at different control rates. Filters generated from discretization of time-continuous filters from a library are applied in different components 404, 406 of the system. The method of FIG. 2, the infrastructure of FIG. 3, or other methods and infrastructures are used to create the filters for the components 404, 406.

The system includes a robot 400, a user console 402, a processor 410, and a memory 412. Additional, different, or fewer devices may be used. For example, addition components and/or distributed parts are provided. In another example, multiple processors and/or memories are used to host the library and/or discretize.

The robot 400 is a robotic arm, robotic manipulator, or other movable or controllable machine. In one embodiment, the robot 400 is one or more robotic arms 4 for use in a surgical or medical environment, such as described above for FIG. 1.

The robot 400 includes one or more components 404, which filter signals. The signals may be sensed or measured information, output control signals, signals being processed, input control signals, communications signals, or any other signals used by the robot 400 for operation, simulation, or fault handling.

The component 404 is a processor, such as a digital signal processor. The component 404 may be a programmable processor, field programmable gate array, or generic processor. Alternatively, the component 404 is an application specific integrated circuit, digital filter, or firmware operable device. The component 404 implements a filter realization to filter the signals.

The signals and/or operation of the component 404 are at the control rate. The filter is operable to filter at the control rate. Different components and/or modes of operation may result in different control rates.

The user console 402 is configured by hardware and/or software to receive user input for control of the robot 400. The user console 402 is a user input device, such as a joystick, computer with keyboard and mouse, or virtual reality device. In one embodiment, the user console 402 is a control console 2 for a robotic surgical system as shown in FIG. 1. The user console 402 connects wirelessly or through wires to the robot 400 to control and receive feedback from the robot 400.

The user console 402 includes one or more components 406, which filter signals. The signals may be sensed or measured information, output control signals, signals being processed, input control signals, communications signals, or any other signals used by the user console 402 for operation, simulation, or fault handling.

The component 406 is a processor, such as a digital signal processor. The component 406 may be a programmable processor, field programmable gate array, or generic processor. Alternatively, the component 406 is a digital filter or firmware operable device. The component 406 implements a filter realization to filter the signals.

The signals and/or operation of the component 406 are at a control rate. The filter is operable to filter at the control rate. Different components and/or modes of operation may result in different control rates. For example, the component 406 has a control rate different than the control rate of the component 404.

The robot 400 and/or user console 402, including the respective components 404, 406 form a distributed system. Rather than a single component, multiple separate components subject to different control rates (e.g., using different clocks) are provided. The robot 400 and/or user console 402 may be operable in different modes. For the surgical robotic system example, the different modes may be a clinical mode for operation on a patient, in a simulation mode for simulating operation on a patient, and in a standalone mode for failure in communications between the surgical robot 400 and the user console 402. The active components of the system change depending on the various system and/or sub-system modes. In these modes, system functionality is often duplicated to meet operational requirements or is redundantly implemented for fault detection or handling. Depending on hardware specifications or computational limitations, the various underlying control algorithms implemented as firmware or software may need to run at various different control rates.

The memory 412 stores the library of filters defined in a continuous domain, such as the library 301 of FIG. 3. In one embodiment, the filters are defined in the continuous domain as s-domain transfer functions with defined or definable transfer functions, cut-off frequencies, attenuations, bandwidths, and/or orders. Any or all characteristics of the filters may be defined or definable.

The memory 412 may be a graphics processing memory, a video random access memory, a random-access memory, system memory, cache memory, hard drive, optical media, magnetic media, flash drive, buffer, database, combinations thereof, or other now known or later developed memory device for storing data. The memory 412 is part of the robot 400, the user console 402, a computer with the processor 410, a standalone device, or memory in another location or device.

The memory 412 or other memory is alternatively or additionally a non-transitory computer readable storage medium storing data representing instructions executable by the programmed processor 410, component 404, or component 406. The instructions for implementing the processes, methods and/or techniques discussed herein are provided on non-transitory computer-readable storage media or memories, such as a cache, buffer, RAM, removable media, hard drive or other computer readable storage media. Non-transitory computer readable storage media include various types of volatile and nonvolatile storage media. The functions, acts or tasks illustrated in the figures or described herein are executed in response to one or more sets of instructions stored in or on computer readable storage media. The functions, acts or tasks are independent of the particular type of instructions set, storage media, processor or processing strategy and may be performed by software, hardware, integrated circuits, firmware, micro code and the like, operating alone, or in combination. Likewise, processing strategies may include multiprocessing, multitasking, parallel processing, and the like.

In one embodiment, the instructions are stored on a removable media device for reading by local or remote systems. In other embodiments, the instructions are stored in a remote location for transfer through a computer network or over telephone lines. In yet other embodiments, the instructions are stored within a given computer, CPU, GPU, or system.

The processor 410 is a general processor, central processing unit, control processor, graphics processor, digital signal processor, three-dimensional rendering processor, application specific integrated circuit, field programmable gate array, digital circuit, combinations thereof, or other now known or later developed device for generating the library of filters, converting filters from continuous time domain to digital time domain, and/or realizing a filter from a discretization. The processor 410 is a single device or multiple devices operating in serial, parallel, or separately. The image processor 410 may be a main processor of a computer, such as a laptop or desktop computer, or may be a processor for handling some tasks in a larger system, such as in the robot 400 or user console 402. The processor 410 is configured by instructions, design, hardware, and/or software to perform the acts discussed herein.

The processor 410 is configured to discretize filters from the library at the desired control rates. Different filters or the same filter are converted to a z- or discrete-time domain based on different control rates. The processor 410 is configured to generate discrete time realizations of the discretized filters. For example, filters are converted from the continuous time to z-domain transfer functions. The z-domain transfer functions are realized by the processor 410 as linear system realizations.

The realized filters are provided to the components 404, 406 for filtering and operation of the robot 400 and user console 402. Alternatively, the signals from the components 404, 406 are provided to the processor 410 for filtering, and the processor 410 provides the filtered results to the component 404, 406 for operation of the robot 400 and user console 402.

The above description of illustrated embodiments of the invention, including what is described below in the Abstract, is not intended to be exhaustive or to limit the invention to the precise forms disclosed. While specific embodiments of, and examples for, the invention are described herein for illustrative purposes, various modifications are possible within the scope of the invention, as those skilled in the relevant art will recognize. These modifications can be made to the invention in light of the above detailed description. The terms used in the following claims should not be construed to limit the invention to the specific embodiments disclosed in the specification. Rather, the scope of the invention is to be determined entirely by the following claims, which are to be construed in accordance with established doctrines of claim interpretation.

What is claimed is:

1. A method for filtering information in a surgical robotic system, the method comprising:
   generating a first filter defined as a continuous domain transfer function, the filter generated based on a filtering requirement;
   discretizing the first filter based on a sample rate for the information in the surgical robotic system, the sample rate being based on an operating mode of the surgical robotic system;
   filtering the information at the sample rate using the discretized first filter; and
   operating the surgical robotic system with the filtered information.

2. The method of claim 1 wherein generating comprises generating the first filter as a s-domain transfer function independent of the sample rate.

3. The method of claim 1 wherein generating comprises generating a library of filters including the first filter, the filters of the library including filters of different types.

4. The method of claim 3 wherein generating the library comprises translating filter definitions based on requirements into the continuous domain transfer functions.

5. The method of claim 1 wherein discretizing comprises forming a z-domain transfer function as a discrete time transfer function at the sample rate.

6. The method of claim 1 wherein discretizing comprises bilinear, bilinear with prewarp, or matched substitution of a continuous time variable of the first filter.

7. The method of claim 1 wherein filtering comprises realizing the first filter as a convolution of the information with a linear system realization of the first filter.

8. The method of claim 1 wherein filtering comprises convolving as a controllable, observable, or time series with input-output form.

9. The method of claim 1 wherein filtering comprises filtering with shift operations.

10. The method of claim 1 further comprising discretizing a second filter based on a different sample rate in the surgical robotic system, filtering signals at the different sample rate with a linear system realization of the second filter, and operating the surgical robotic system with the filtered signals from the second filter.

11. The method of claim 10 wherein the surgical robotic system comprises a distributed system wherein the filtering of the information is performed for a first component of the distributed system and the filtering of the signals is performed for a second component of the distributed system.

12. The method of claim 1 wherein discretizing comprises discretizing with the sampling rate being based on the operating mode comprising one of a clinical mode, a simulation mode, or a standalone mode.

13. A surgical robotic system for filtering at different control rates, the surgical robotic system comprising:
   a surgical robot having a first component operable at a first control rate;
   a user console configured to receive user input for control of the surgical robot, the user console connected wirelessly or through wires to the surgical robot, the user console having a second component operable at a second control rate different than the first control rate;

a memory storing a library of filters defined in a continuous domain; and a processor configured to discretize a first filter from the library with the first control rate and a second filter from the library with the second control rate, the processor configured to generate discrete time realizations of the first and second filters.

14. The surgical robotic system of claim 13 wherein the first component is configured to apply the first filter and the second component is configured to apply the second filter.

15. The surgical robotic system of claim 13 wherein the surgical robot and the user console are operable in a clinical mode for operation on a patient, in a simulation mode for simulating operation on a patient, and in a standalone mode for failure in communications between the surgical robot and the user console.

16. The surgical robotic system of claim 13 wherein the filters defined in the continuous domain comprise s-domain transfer functions with defined transfer functions, cut-off frequencies, attenuations, bandwidths, and orders, wherein the first and second filters as discretized comprise z-domain transfer functions, and wherein the discrete time realizations of the first and second filters comprise linear system realizations.

17. A method for scalable filtering infrastructure, the method comprising:

inputting filter requirements for filtering at a first control rate, the first control rate based on operation of a surgical robotic system;

selecting a filter from a library of filters based on the requirements, the filters of the library being independent of the first control rate and defined in a continuous time mode;

converting the selected filter to the first control rate;

generating a filter kernel for the converted filter; and filtering digital signals with the filter kernel at the first control rate.

18. The method of claim 17 wherein inputting comprises a designer inputting the filter requirements for a component of the surgical robotic system that operates at the first control rate, the filter requirements including an order limited by memory requirements.

19. The method of claim 17 wherein the filter comprises a first filter and the digital signals comprise first signals, and wherein filtering comprises filtering the first signals by a first processor of the surgical robotic system with distributed components, the first processor in a first component of the distributed components, and further comprising repeating the inputting, selecting, converting, generating, and filtering for a second filter at a second control rate different than the first control rate, second signals for the second filter being in a second component of the distributed components.

20. The method of claim 17 wherein converting comprises discretizing the filter from the continuous time mode to a discrete time domain at the first control rate, and wherein generating comprises performing linear system realization from the discrete time domain.

* * * * *